(12) United States Patent
Watanabe

(10) Patent No.: US 10,307,239 B2
(45) Date of Patent: Jun. 4, 2019

(54) FILTER DEVICE

(71) Applicant: NIPRO CORPORATION, Osaka-shi, Osaka (JP)

(72) Inventor: Hiroki Watanabe, Osaka (JP)

(73) Assignee: NIPRO CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 15/303,440

(22) PCT Filed: Apr. 7, 2015

(86) PCT No.: PCT/JP2015/060849
§ 371 (c)(1),
(2) Date: Oct. 11, 2016

(87) PCT Pub. No.: WO2015/159759
PCT Pub. Date: Oct. 22, 2015

(65) Prior Publication Data
US 2017/0035545 A1 Feb. 9, 2017

(30) Foreign Application Priority Data

Apr. 15, 2014 (JP) .................................. 2014-083486
Oct. 21, 2014 (JP) .................................. 2014-214562
Nov. 6, 2014 (JP) .................................. 2014-225759

(51) Int. Cl.
*A61F 2/01* (2006.01)
*A61B 90/00* (2016.01)
*A61M 25/01* (2006.01)

(52) U.S. Cl.
CPC ................ *A61F 2/01* (2013.01); *A61B 90/39* (2016.02); *A61F 2002/011* (2013.01);
(Continued)

(58) Field of Classification Search
CPC .................. A61F 2/01; A61F 2002/015; A61F 2002/016; A61F 2002/011
See application file for complete search history.

(56) References Cited

U.S. PATENT DOCUMENTS 6,066,149 A 5/2000 Samson et al.
6,152,946 A 11/2000 Broome et al.
(Continued)

FOREIGN PATENT DOCUMENTS

JP 2001-522639 A 11/2001
JP 2002-505151 A 2/2002
(Continued)

OTHER PUBLICATIONS

International Search Report issued in International Patent Application No. PCT/JP2015/060849 dated Jun. 30, 2015.
(Continued)

*Primary Examiner* — Diane D Yabut
(74) *Attorney, Agent, or Firm* — Foley & Lardner LLP

(57) ABSTRACT

A filter device has a catheter having a lumen, a shaft extended in the longitudinal direction from the lumen, and a filter capturing an embolus. The filter is connected to the shaft through a slide ring at the distal end thereof. The shaft is inserted into and passed through the ring. The ring is rotatable with respect to the shaft and slidable in the longitudinal direction. When the filter is expanded in a blood vessel, the ring slides on the shaft. The filter is connected to the shaft through another ring on the peripheral edge of an opening. The shaft is inserted into and passed through the ring. The ring is rotatable with respect to the shaft. The ring is held between a pair of stoppers fixed onto the shaft. Therefore, the movement of the ring in the longitudinal direction with respect to the shaft is prevented.

6 Claims, 10 Drawing Sheets

(52) U.S. Cl.
CPC ... *A61F 2002/015* (2013.01); *A61F 2002/016* (2013.01); *A61F 2230/0067* (2013.01); *A61F 2250/0032* (2013.01); *A61F 2250/0098* (2013.01); *A61M 25/0108* (2013.01)

(56) References Cited

U.S. PATENT DOCUMENTS

| | | | |
|---|---|---|---|
| 6,383,205 | B1 | 5/2002 | Samson et al. |
| 6,558,405 | B1 | 5/2003 | McInnes |
| 7,399,308 | B2 | 7/2008 | Borillo et al. |
| 7,621,870 | B2 | 11/2009 | Berrada et al. |
| 7,875,050 | B2 | 1/2011 | Samson et al. |
| 8,092,486 | B2 | 1/2012 | Berrada et al. |
| 8,486,104 | B2 | 7/2013 | Samson et al. |
| 8,777,976 | B2 | 7/2014 | Brady et al. |
| 8,956,384 | B2 | 2/2015 | Berrada et al. |
| 2002/0082558 | A1 | 6/2002 | Samson et al. |
| 2002/0138094 | A1 | 9/2002 | Borillo et al. |
| 2002/0188314 | A1 | 12/2002 | Anderson et al. |
| 2003/0060844 | A1 | 3/2003 | Borillo et al. |
| 2003/0176884 | A1 | 9/2003 | Berrada et al. |
| 2004/0039412 | A1 | 2/2004 | Isshiki et al. |
| 2004/0172055 | A1* | 9/2004 | Huter ............... A61F 2/013 606/200 |
| 2005/0283186 | A1 | 12/2005 | Berrada et al. |
| 2006/0030878 | A1 | 2/2006 | Anderson et al. |
| 2007/0073332 | A1 | 3/2007 | Miller et al. |
| 2008/0172084 | A1* | 7/2008 | Kusleika ............ A61F 2/01 606/201 |
| 2010/0042136 | A1 | 2/2010 | Berrada et al. |
| 2011/0082493 | A1 | 4/2011 | Samson et al. |
| 2011/0125181 | A1* | 5/2011 | Brady ............ A61B 17/22031 606/200 |
| 2012/0083824 | A1 | 4/2012 | Berrada et al. |
| 2013/0144326 | A1 | 6/2013 | Brady et al. |
| 2013/0184739 | A1 | 7/2013 | Brady et al. |
| 2014/0249571 | A1 | 9/2014 | Tsutsui et al. |
| 2014/0379023 | A1 | 12/2014 | Brady et al. |

FOREIGN PATENT DOCUMENTS

| | | |
|---|---|---|
| JP | 2002-505151 A5 | 2/2002 |
| JP | 2003-521259 A | 7/2003 |
| JP | 2003-521259 A5 | 7/2003 |
| JP | 2003-220062 A | 8/2003 |
| JP | 2004-097807 A | 4/2004 |
| JP | 2007-117760 A | 5/2007 |
| JP | 2007-130116 A | 5/2007 |
| JP | 2007-325893 A | 12/2007 |
| JP | 2009-268648 A | 11/2009 |
| JP | 2013-085657 A | 5/2013 |
| WO | WO-99/23976 A1 | 5/1999 |
| WO | WO-01/52768 A1 | 7/2001 |

OTHER PUBLICATIONS

Extended European Search Report in corresponding application No. 15779668.1 dated Oct. 27, 2017.

* cited by examiner

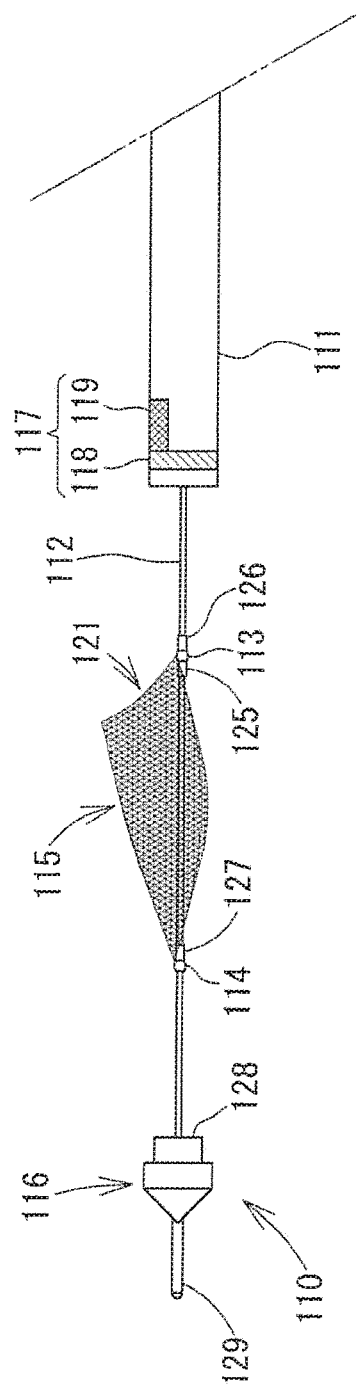

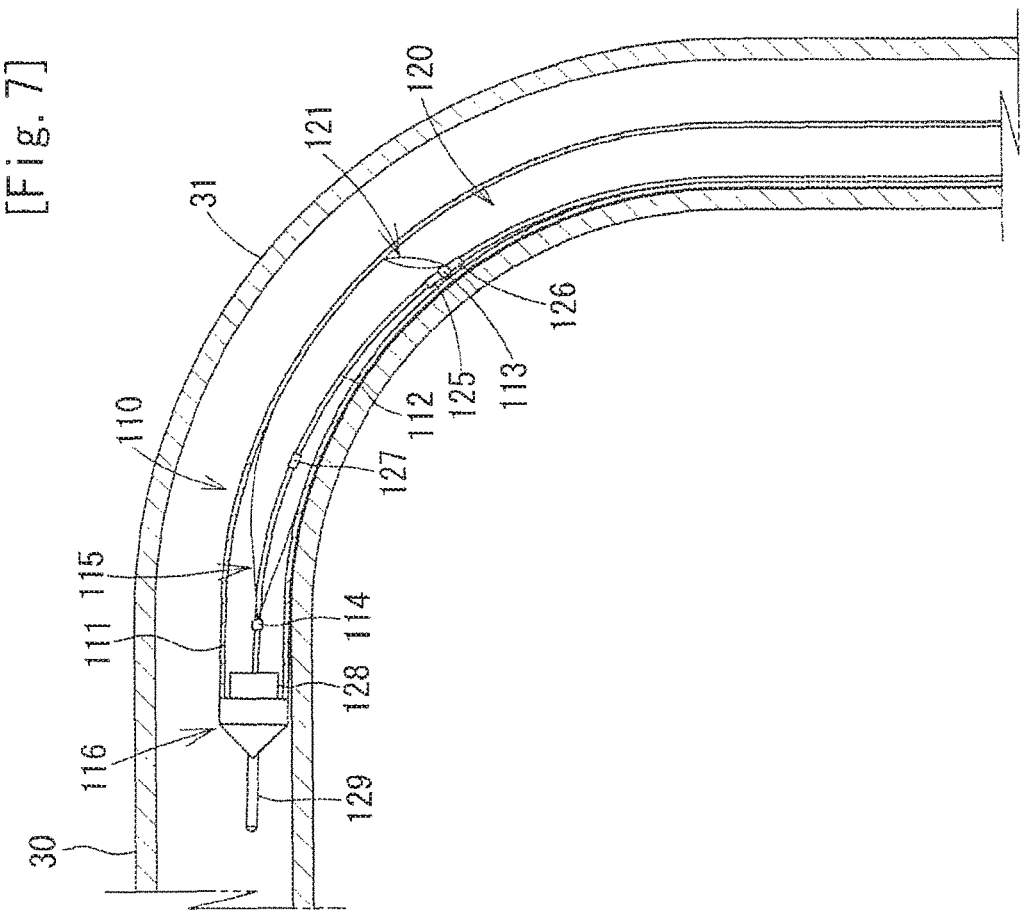

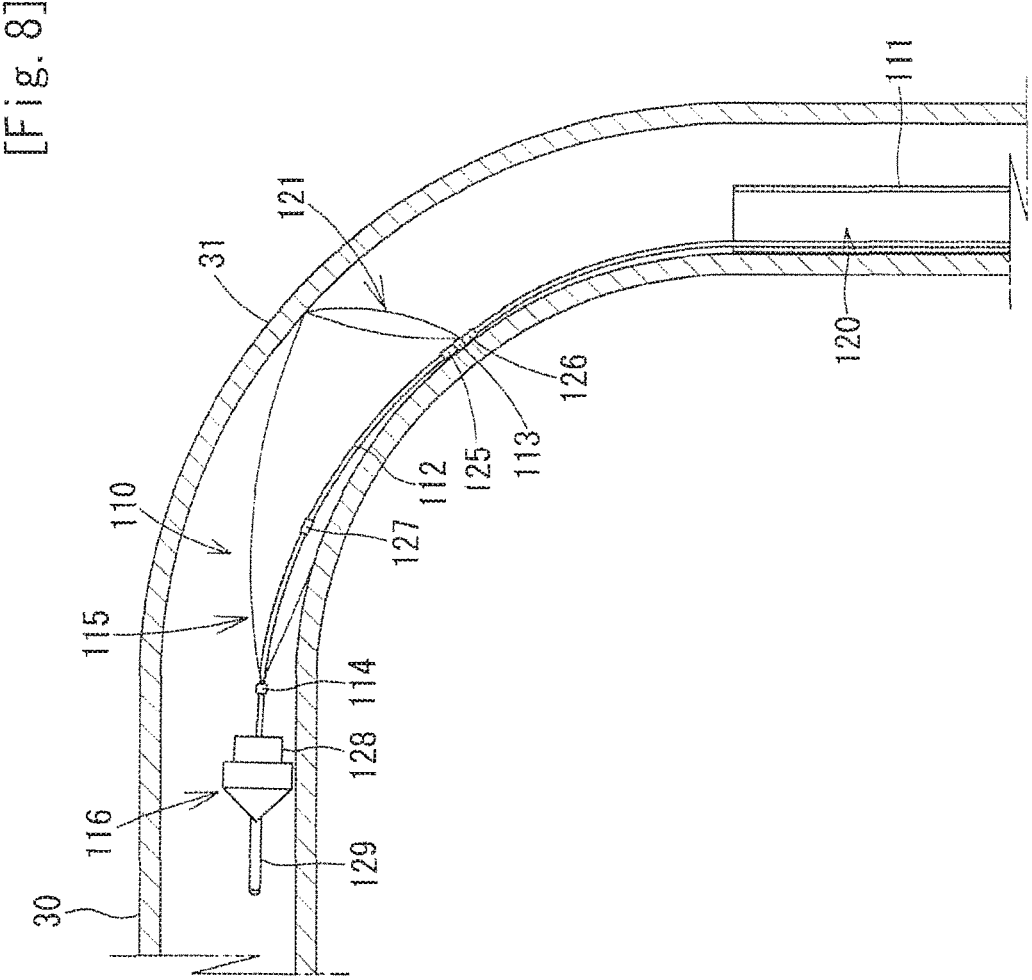

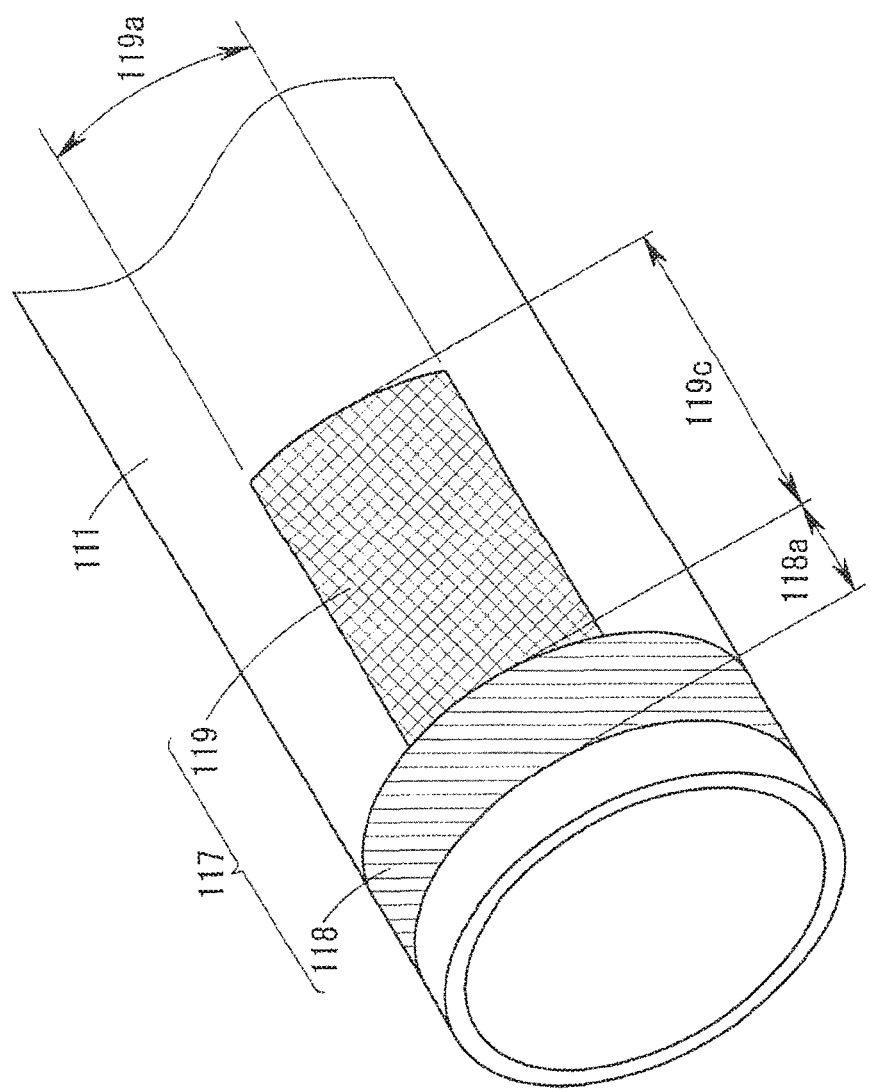

[Fig. 10]
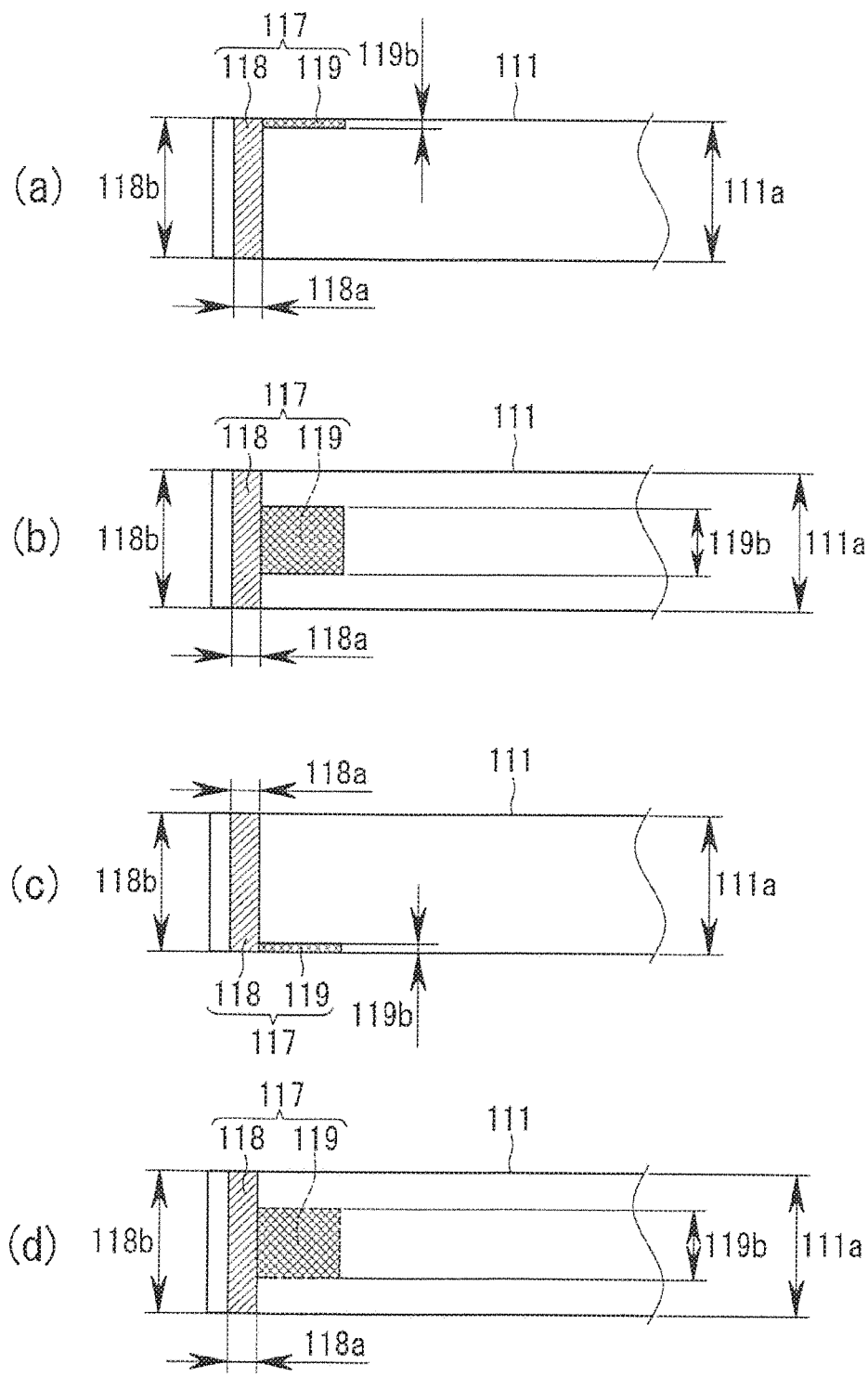

FILTER DEVICE

CROSS-REFERENCE TO RELATED APPLICATIONS

The present application is a U.S. national stage application of International Patent Application No. PCT/JP2015/060849, filed Apr. 7, 2015, which claims the benefit of priority to Japanese Patent Application No. 2014-083486, filed Apr. 15, 2014; Japanese Patent Application No. 2014-214562, filed Oct. 21, 2014; and Japanese Patent Application No 2014-225759, filed Nov. 6, 2014, the entireties of which are all hereby incorporated by reference.

TECHNICAL FIELD

The present invention relates to a filter device having a filter placed in a blood vessel.

BACKGROUND ART

In a state where a stent is indwelled in a carotid artery region, when some plaques and thrombi flow into the peripheral side of the carotid artery, there is a possibility that the plaques and the thrombi are clogged into a cerebral blood vessel to cause cerebral infarction. In order to avoid the possibility, filters to be set in a blood vessel have been known heretofore as those capturing some plaques and thrombi without blocking the blood flow to the peripheral side relative to a stenosis portion of a blood vessel.

A filter described in Patent Literature 1 is provided with a distal end side slider and a proximal end side slider at the distal end and the proximal end, respectively, of the filter and the distal end side slider and the proximal end side slider are slidably inserted into and passed through a guide wire independently from each other. In the guide wire, a stopper is provided between the distal end side slider and the proximal end side slider. The stopper can abut on each of the distal end side slider and the proximal end side slider. Thus, the filter is movable to the proximal end side of the guide wire until the distal end side slider abuts on the stopper and is movable to the distal end side of the guide wire until the proximal end side slider abuts on the stopper.

The filter is inserted into a blood vessel through an introducer catheter. The filter housed in the introducer catheter is in a state where the distal end side slider and the proximal end side slider are separated from each other and the filter is contracted along the guide wire. Due to the fact that the filter is exposed from the introducer catheter, the distal end side slider and the proximal end side slider are brought close to each other, and then the filter which is elastically returned is expanded in the radial direction.

Patent Literature 2 discloses a filter device having a filter which has a bag shape having an opening portion formed at the distal end and having a closed proximal end and the filter which has a large number of small holes formed in the peripheral wall. In the filter, an opening portion holding wire is provided along the circumference of the opening portion and a marker coil is spirally wound around the opening portion holding wire. The opening portion holding wire has elasticity, and thus is deformable into a circular shape (ring shape) and a non-circular shape. The opening portion of the filter is deformed according to the deformation of the opening portion holding wire.

The filter is moved through the inside of a blood vessel in a state where the filter is housed in a sheath. In this case, the opening portion holding wire is contracted in a non-circular shape along the blood vessel in the sheath. When the sheath reaches a desired position in a blood vessel, the filter is drawn out of the sheath. Thus, the opening portion holding wire is expanded in a circular shape while being inclined with respect to the blood flow direction in the blood vessel, so that the opening portion of the filter is changed to the same shape. In the change, the position of the opening portion of the filter on an X-ray fluoroscopic screen is confirmed by the marker coil wounded around the opening portion holding wire.

A filter described in Patent Literature 3 has a conical shape, has an opening on the side of a proximal end portion, and has a tapered shape toward the side of a terminal end. The filter is fixed to a wire at each of the terminal end portion and the proximal end portion. The filter in an expanded state does not have a symmetrical shape with respect to the wire as the axis line.

A catheter described in Patent Literature 4 has two guide wire tubes for inserting a guide wire into each of branched blood vessels. Each tube has a marker at a predetermined position near the distal end. The marker is formed with a material which does not allow the transmission of X-rays. The shape of the marker is a ring shape or a ring shape having a notch. By X-ray imaging of the blood vessel into which the catheter is inserted, the marker can be visually recognized and the directions and the distal end positions of the two tubes can be grasped by the shape of the markers.

CITATION LIST

Patent Literatures

Patent Literature 1: Japanese Unexamined Patent Application Publication No. 2007-117760
Patent Literature 2: Japanese Unexamined Patent Application Publication No. 2013-85657
Patent Literature 3: Japanese Unexamined Patent Application Publication (Translation of PCT Application) No. 2002-505151
Patent Literature 4: Japanese Unexamined Patent Application Publication No. 2007-130116

SUMMARY OF INVENTION

Technical Problems

In the case of the catheter described in Patent Literature 1, even when the filter is inserted into a blood vessel to be located at a desired position while confirming the position of the distal end side slider or the proximal end side slider by X-rays, and then the filter is exposed from the introducer catheter, the filter in an expanded state is movable to the distal end side or the proximal end side along the guide wire until the distal end side slider or the proximal end side slider abuts on the stopper, and therefore positional deviation from the position confirmed by X-rays to the distal end side or the proximal end side may occur. For example, even when it is attempted to place the filter on the upstream side immediately before a blood vessel is branched, the filter may be expanded on the downstream side relative to the branched portion due to the positional deviation.

By the marker coil described in Patent Literature 2, the position of the opening portion of the filter can be confirmed by an X-ray fluoroscopic screen but it is difficult to confirm whether the filter is in a contracted state or an expanded state. For example, even when the opening portion of the filter is expanded in a circular shape, the opening portion is sometimes recognized as an oval shape or a linear shape depending on the angle of the opening portion observed on the X-ray fluoroscopic screen, and therefore it is hard to discriminate whether the filter is in a contracted state or in an expanded state. When the filter is expanded in a portion where a blood vessel is curved or the like, the filter may be also curved along the curve of the blood vessel, so that the shape and the angle of the opening portion of the filter expanded at the curved portion may be different from the shape and the angle of the opening portion of the filter expanded at a linear portion of the blood vessel.

When the filter described in Patent Literature 3 is placed in a portion where a blood vessel is curved, a case occurs where the opening portion of the filter is narrowed depending on the direction where the filter is expanded with respect to the wire, i.e., the position of the filter with respect to the wire. In the portion where the blood vessel is curved, when the wire fixing the filter is located on the outside of the curve of the blood vessel and the filter is located on the inside of the curve, the filter is pressed out to the inner side of the curve of the blood vessel due to the elastic restoring force of the wire located on the outside of the curve. As a result, the opening portion of the filter is compressed, so that the projected area in a cross section of the blood vessel is narrowed. On the other hand, when the wire is located on the inside of the curve of the blood vessel and the filter is located on the outside of the curve, the wire does not press the filter to the outside of the curve of the blood vessel, and therefore the case where the opening portion is compressed as described above is hard to occur. Therefore, it is desirable to grasp the direction where the filter is expanded with respect to the wire in the blood vessel.

In the case of the catheter described in Patent Literature 4, the position and the direction of the distal end of each of the two tubes can be grasped based on the position and the shape of the marker provided on each tube. However, in Patent Literature 4, the layout of the two tubes is predicted to some extent and the position of each tube to be grasped with respect to the branch of the blood vessel is restrictive. More specifically, each marker is located on the axis line of each tube in a state where the two tubes are disposed in the vertical direction, for example, and therefore the markers are not located on the same line. The markers are disposed apart from each other in the axial direction. More specifically, the marker marked on the tube linearly guiding the guide wire is located on the front side in the insertion direction and the marker marked on the tube guiding the guide wire in a curved manner is located on the rear side in the insertion direction, and therefore it can be grasped whether each tube is present on either the upper or lower side, i.e., the direction of the two tubes. On the other hand, in a state where the two tubes are overlapped in the gaze direction, the markers are located on the same line. However, in order to confirm the branched blood vessels by imaging, the blood vessel needs to be branched in the vertical direction. Therefore, the state where the two tubes are overlapped with each other is judged to be a state where the guide wire cannot be guided to the branched blood vessels. Thus, in Patent Literature 4, a direction suitable for guiding the guide wire to the branched blood vessels is discriminated based on the position and the shape of the markers in the structure where the two tubes are disposed side by side. Therefore, the marker described in Patent Literature 4 is not suitable for grasping a direction in which a filter housed in one catheter is expanded as in Patent Literature 3.

The present invention has been made in view of the circumstances as described above. It is an object of the present invention to provide a filter device capable of certainly placing a filter at a desired position of a blood vessel.

It is another object of the present invention to provide a means by which it is easily confirmed that a filter is in an expanded state.

It is still another object of the present invention to provide a filter device capable of easily judging a direction where a filter housed in a catheter is expanded with respect to a wire material at a desired position of a blood vessel.

Solution to Problems (1) A filter device according to the present invention has a catheter having a housing space inside, a wire material extended along the longitudinal direction of the catheter in the housing space of the catheter, a filter capable of changing the state between an expanded state in which the filter is exposed to the distal end side of the catheter to be expanded to the outer side relative to the outer shape of the catheter and a contracted state in which the filter is elastically contracted from the expanded state so as to be housed in the housing space, a slider which is provided on the distal end side of the filter, rotatable about the wire material as the axis, and movable along the wire material, and a proximal end side fixing portion which is provided on the proximal end side of the filter, rotatable about the wire material as the axis, and prevented from moving in the longitudinal direction with respect to the wire material.

The catheter is inserted into a blood vessel until the distal end of the catheter reaches a desired position of the blood vessel in a state where the filter in the contracted state is housed in the housing space of the catheter. When the distal end of the catheter reaches the desired position, the catheter is drawn back to the proximal end side with respect to the wire material to be exposed from the distal end of the catheter. The movement of the proximal end side of the filter in the longitudinal direction with respect to the wire material is prevented by the proximal end side fixing portion. Due to the fact that the filter is elastically changed to the expanded state from the contracted state, the slider is brought close to the proximal end side fixing portion. Since both the slider and the proximal end side fixing portion are rotatable about the wire material as the axis, the filter in the expanded state rotates with respect to the wire material following the inner wall shape of the blood vessel.

(2) Preferably, the filter device further has a first stopper fixed to the wire material between the slider and the proximal end side fixing portion.

For example, when the wire material is pressed to the distal end side, the proximal end side of the filter may be twisted. However, the abutting of the slider on the stopper prevents the slider from moving closer to the proximal end side fixing portion more than necessary to excessively bend or damage the filter.

(3) Preferably, the proximal end side fixing portion has a tubular body rotatably provided on the wire material and second stoppers individually fixed to the wire material on the distal end side and the proximal end side with respect to the tubular body.

Thus, the proximal end side fixing portion can be realized with a simple structure.

(4) Preferably, the filter has a conical shape which has an opening on the proximal end side and in which the diameter decreases toward the distal end side.

Thus, the filter is easily expanded along the internal diameter and the shape of the blood vessel.

(5) Preferably, the slider and the proximal end side fixing portion are detectable by radiation.

Thus, the set position of the filter in the blood vessel can be confirmed.

(6) A filter device according to the present invention has a catheter having a housing space inside, a wire material extended along the longitudinal direction of the catheter in the housing space of the catheter, and a filter capable of changing the state between an expanded state in which the filter is exposed to the distal end side of the catheter to be expanded to the outer side relative to the outer shape of the catheter and a contracted state in which the filter is elastically contracted from the expanded state so as to be housed in the housing space, in which the filter in the expanded state has an opening on one side in the longitudinal direction and has a peripheral wall formed with a plurality of thin wires forming a net shape, and at least one of the thin wires contains a radiation ray detection material detectable by radiation.

The filter in the expanded state in the blood vessel can be judged to be in the expanded state by discriminating the shape of the thin wires containing the radiation ray detection material in the filter in the expanded state in a radioscopic image obtained by emitting radiation.

(7) Preferably, the thin wires containing the radiation ray detection material form a spiral shape along the longitudinal direction in the expanded state.

Such a configuration makes it possible to more accurately confirm by the thin wires containing the radiation ray detection material that the filter is in the expanded state in a radioscopic image.

(8) Preferably, the thin wires containing the radiation ray detection material include at least two or more thin wires and cross to each other.

Thus, it can be much more accurately confirmed that the filter is in the expanded state.

(9) Preferably, the thin wire containing the radiation ray detection material has a first wire having a shape memory property and a second wire which does not allow transmission of radiation or attenuates radiation and which is wound around the outside of the first wire.

Due to such a configuration, the change when the first wire is returned to the memorized shape is hardly blocked by the second wire.

(10) Preferably, in the thin wire containing the radiation ray detection material, a first wire having a shape memory property is plated with a metal which does not allow transmission of radiation or attenuates radiation.

Thus, the first wire having a shape memory property is detectable by radiation.

(11) Preferably, the thin wire containing the radiation ray detection material does not allow transmission of radiation or attenuates radiation.

(12) A filter device according to the present invention has a tubular catheter having a housing space inside, a wire material extended along the longitudinal direction of the catheter in the housing space of the catheter, a first support portion provided on the wire material, a second support portion provided on the wire material, a filter which is supported by the first support portion and the second support portion and is disposed along the wire material and which has an outer shape changeable to a contracted state in which the filter can be housed in the housing space and an expanded state in which the filter is expanded to the outer side relative to the outer shape of the catheter on the outside of the housing space of the catheter, and a marker provided on the catheter and detectable by X-rays. In the filter, an end portion on the side of the second support portion is closed and an end portion on the side of the first support portion is opened in the expanded state, the first support portion is disposed at a position other than the center of the opening of the filter in the expanded state, and the marker has a first portion continuous along the circumferential direction and a second portion extended along the longitudinal direction from a part in the circumferential direction of the first portion on the external surface of the catheter.

The filter in the contracted state is housed in the housing space of the catheter in an arbitrary direction with respect to the marker. The catheter is inserted into a blood vessel until the filter reaches a desired position of the blood vessel in the state where the filter is housed in the housing space of the catheter. The direction of the filter which is caused to reach the desired position is adjusted by rotating the catheter about the longitudinal direction of the catheter as the axis. The position and the direction of the catheter are adjusted by confirming the position and the shape of the first portion and the second portion of the marker detected by X-rays from one direction in the radial direction of the catheter. When the distal end of the catheter is disposed at a desired position and in a desired direction, the filter is exposed to the outside of the catheter from the distal end of the catheter. At the desired position of the blood vessel, the filter is elastically changed to the expanded state. Thus, the filter is placed in an arbitrary direction at the desired position of the blood vessel.

(13) Preferably, the filter in the contracted state rotates in connection with the rotation about the longitudinal direction of the catheter as the axis due to contact of the filter with the inner surface defining the housing space of the catheter.

Thus, the catheter and the filter are integrally rotated while holding the relative positional relationship in the state where the filter is housed in the housing space of the catheter without providing a member for holding the positional relationship of the filter and the catheter. In other words, the direction of the filter with respect to the marker provided on the catheter is held in a fixed direction only by the catheter and the filter.

(14) Preferably, the first portion is formed of metal and the second portion is formed of resin.

Since the second portion is formed of resin, the flexibility of the distal end portion of the catheter is not impaired.

(15) Preferably, a raw material of the second portion is a resin containing an inorganic material detectable by X-rays.

(16) Preferably, the length along the circumferential direction of the second portion is fixed.

(17) Preferably, the length along the circumferential direction of the second portion is shorter than the half of the length of the circumference along the circumferential direction of the external surface of the catheter.

Thus, the position in the circumferential direction of the second portion is easily grasped. Moreover, the flexibility of the distal end portion of the catheter is not impaired.

(18) Preferably, the length along the longitudinal direction of the second portion is longer than the maximum length along the longitudinal direction of the first portion.

Thus, the first portion and the second portion can be easily distinguished from each other.

(19) Preferably, the length along the longitudinal direction of the first portion is fixed.

Advantageous Effects of Invention

According to the present invention, a filter can be certainly placed at a desired position of a blood vessel without causing positional deviation.

Moreover, according to the present invention, it can be certainly confirmed by a radioscopic image that the filter is in the expanded state in a blood vessel.

Moreover, according to the present invention, the direction of the filter with respect to the wire material in a state of being housed in the catheter at a desired position of a blood vessel can be easily judged. As a result, the position of the filter with respect to the wire material at a bent portion or the like of a blood vessel can be easily adjusted.

BRIEF DESCRIPTION OF DRAWINGS

FIG. 6 is a view illustrating the external configuration of a filter device 110 according to a third embodiment.

FIG. 7 is a view illustrating a state where a filter 115 is contracted and a catheter 111 is inserted into the blood vessel 30.

FIG. 8 is a view illustrating a state where the filter 115 is expanded in the blood vessel 30.

FIG. 9 is a perspective view illustrating a marker 117 formed in the catheter 111.

FIGS. 10(a) to 10(d) are views schematically illustrating the marker 117 formed on the catheter 111.

DESCRIPTION OF EMBODIMENTS

Hereinafter, preferable embodiments of the present invention are described. The embodiments merely describe one embodiment of the present invention. It is a matter of course that the embodiments can be altered insofar as the scope of the present invention is not altered.

First Embodiment

Figure 1:
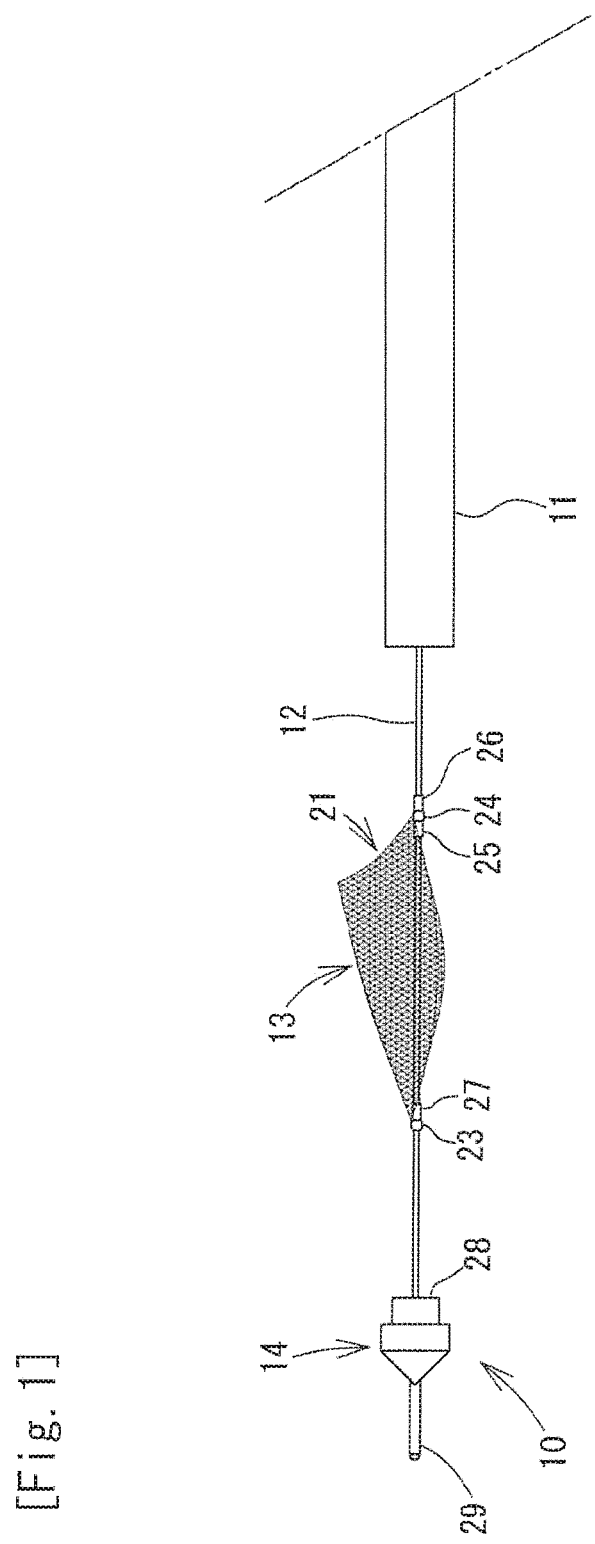
FIG. 1 is a view illustrating the external configuration of a filter device 10 according to a first embodiment.
Figure 2:
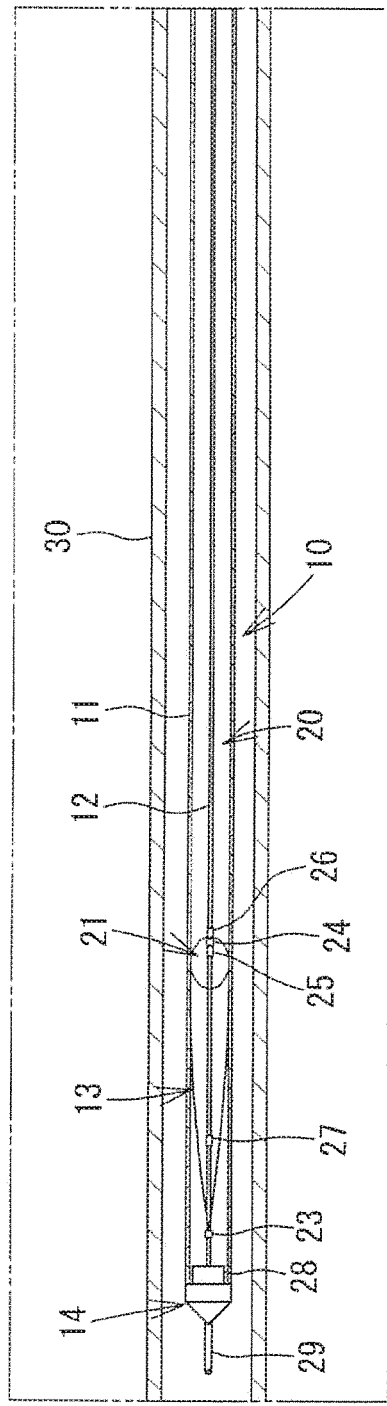
FIG. 2 is a view illustrating a state where a filter 13 is contracted and a catheter 11 is inserted into a blood vessel 30.

As illustrated in FIG. 1, a filter device 10 has a catheter 11, a shaft 12 (an example of the wire material) extended along the longitudinal direction of the catheter 11 in the catheter 11, a filter 13 provided on the distal end side of the shaft 12, and a distal end guide 14 provided at the distal end of the shaft 12. The filter device 10 is inserted into a blood vessel from the distal end side of the catheter 11, and then the filter 13 is exposed from the distal end of the catheter 11, whereby the filter 13 in an expanded state is indwelled at a desired position of the blood vessel. FIG. 1 illustrates the filter device 10 when the filter 13 is in the expanded state. As illustrated in FIG. 2, the filter 13 is housed in a lumen 20 of the catheter 11, and then moved to a desired position of a blood vessel in a contracted state.

The catheter 11 is a tube-shaped member which can be inserted into a target blood vessel and has the lumen 20 (an example of the housing space, refer to FIGS. 2 and 3) passing through the distal end and the proximal end. The catheter 11 has flexibility which allows the catheter 11 to bend along a curve and a branch of a blood vessel. For the catheter 11, for example, flexible synthetic resin tubes of soft vinyl chloride resin, polyolefins, such as polyethylene and polypropylene, an ethylene-propylene copolymer and an ethylene-vinyl acetate copolymer, polyolefin elastomers, such as a mixture of polypropylene and polybutene, polyamide, fluororesin, such as PTFE and ETFE, a polyamide elastomer, a polyester elastomer, a polyurethane elastomer, a fluororesin-based elastomer, and the like; rubber tubes of silicon rubber, latex rubber, and the like; and the like are preferably used. The outer diameter and the length of the catheter 11 are set as appropriate according to the positions of a target blood vessel and a target lesion. Although not illustrated in each view, known configurations, such as a handle portion, for increasing operability may be provided as appropriate at the proximal end of the catheter 11.

The shaft 12 is a wire material extended along the longitudinal direction in the lumen 20 of the catheter 11. The shaft 12 has flexibility which allows the shaft 12 to bend along a curve and a branch of a blood vessel and rigidity which prevents buckling of the distal end side when the proximal end side is pressed in the longitudinal direction. As the shaft 12, a stainless steel wire, a piano wire, high-tensile steel wires for springs, superelastic metal wires, and the like are preferably used. The outer diameter and the length of the shaft 12 are set as appropriate according to the positions of a target blood vessel and a target lesion and the internal diameter and the length of the catheter 11.

The filter 13 is a conical-shaped net-like member which has an opening 21 on the proximal end side and in which the diameter decreases toward the distal end side. The opening 21 has an annular shape having a diameter larger than the diameter of the lumen 20 of the catheter 11. The opening 21 is disposed on the proximal end side of the shaft 12 and is directed in a direction inclined with respect to the axis line (longitudinal direction) of the shaft 12. The distal end of the filter 13 is closed and is directed to the distal end side of the shaft 12. The filter 13 has flexibility which allows the filter 13 to bend so as to be housed in the lumen 20 of the catheter 11. The filter 13 can be housed in the lumen 20 of the catheter 11 in a state where the filter 13 is bent (contracted state). When the filter 13 comes out to the outside of the lumen 20, the filter 13 is elastically returned to be a conical shape (expanded state).

For raw materials of the filter 13, superelastic alloys, such as a nickel-titanium steel wire, high-tensile steel wires for springs, metal wires, such as a piano wire, synthetic resin having relatively high rigidity, such as polyamide and fluororesin, and the like are preferably used, for example. The filter 13 is produced by knitting a linear metal or the like. The size of the filter 13, the diameter of the annular shape of the opening 21, and the like are set as appropriate according to the internal diameter of a target blood vessel and the catheter 11.

The filter 13 is connected to the shaft 12 through slide rings 23 and 24 at the distal end and the peripheral edge of the opening 21, respectively. The slide rings 23 and 24 are ring-shaped members containing members detectable by X-rays, such as stainless steel, and the shaft 12 is inserted into and passed through the internal space thereof. The filter 13 and the slide rings 23 and 24 are bonded to each other by welding or with adhesives. The slide ring 23 (an example of the slider) is rotatable about the shaft 12 as the axis and is slidable in the longitudinal direction with respect to the shaft 12. The distal end of the filter 13 bonded to the slide ring 23 is rotatable about the shaft 12 as the axis together with the slide ring 23 and is slidable in the longitudinal direction with respect to the shaft 12.

The slide ring 24 (an example of the tubular body) is held between a pair of stoppers 25 and 26 (an example of the second stoppers) fixed to the distal end side of the shaft 12. The stoppers 25 and 26 are ring-shaped members containing stainless steel and the like and are fixed to the shaft 12 in a state where the shaft 12 is inserted into and passed through the internal space thereof. The stoppers 25 and 26 do not rotate with respect to the shaft 12 and do not move in the longitudinal direction. The slide ring 24 held between the stoppers 25 and 26 is rotatable about the shaft 12 as the axis and the movement of the slide ring 24 in the longitudinal direction with respect to the shaft 12 is prevented. The peripheral edge of the opening 21 of the filter 13 fixed to the slide ring 24 is rotatable about the shaft 12 as the axis and the movement thereof in the longitudinal direction with respect to the shaft 12 is prevented.

The shaft 12 is provided with a stopper 27 (an example of the first stopper) between the slide rings 23 and 24. The stopper 27 is a ring-shaped member containing a stainless steel or the like and is fixed to the shaft 12 in a state where the shaft 12 is inserted into and passed through the internal space thereof. The stopper 27 does not rotate with respect to the shaft 12 and does not move in the longitudinal direction. The stopper 27 is disposed at a position where the slide ring 24 abuts on or is brought close to the stopper 27 in the filter 13 in the expanded state. Due to the fact the slide ring 24 abuts on the stopper 27, the movement of the slide ring 23 to the slide ring 24 side relative to the position of the stopper 27 is prevented.

The distal end guide 14 is fixed to the distal end of the shaft 12. The distal end guide 14 is projected along the axis line of the shaft 12 from the distal end of the shaft 12. The distal end guide 14 has a fitting portion 28 fitted to the distal end of the catheter 11 and a guide portion 29 projected from the fitting portion 28. The fitting portion 28 contains a synthetic resin. Due to the fact that a part of the fitting portion 28 enters the lumen 20 in the distal end of the catheter 11, the fitting portion 28 is fitted to the catheter 11 in a state where the distal end of the lumen 20 is sealed. The guide portion 29 is obtained by winding stainless steel in a spiral shape and is elastically curved along a curve and a branch of a blood vessel.

[Directions for Use of Filter Device 10]

Figure 3:
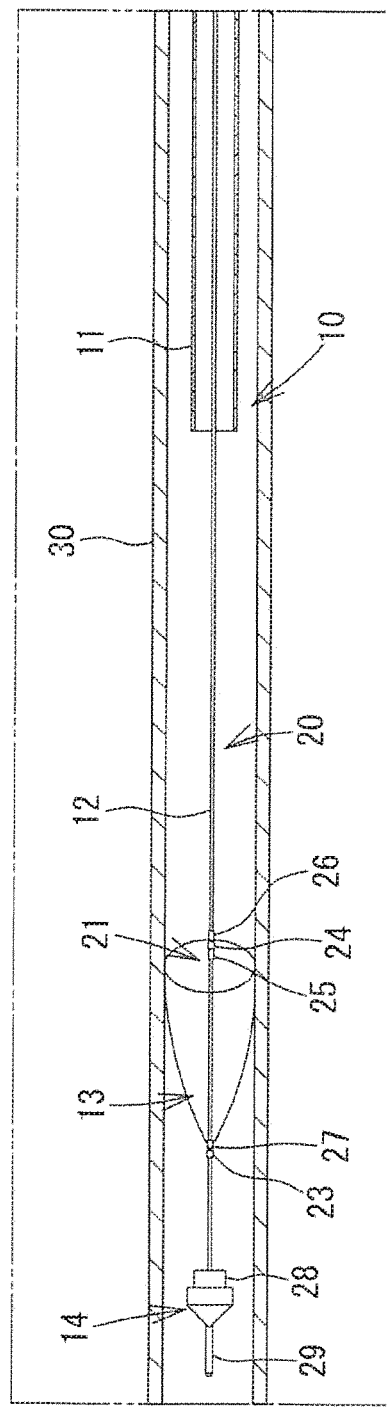
FIG. 3 is a view illustrating a state where the filter 13 is expanded in the blood vessel 30.

Hereinafter, the directions for use of the filter device 10 are described with reference to FIGS. 2 and 3. In FIGS. 2 and 3, only a visible outline is illustrated for the filter 13.

As illustrated in FIG. 2, the filter device 10 is inserted into the blood vessel 30 in a state where the filter 13 is changed to the contracted state to be housed in the lumen 20 of the catheter 11 and the distal end guide 14 is fitted to the distal end of the catheter 11. The filter device 10 is inserted into the blood vessel 30 from the distal end guide 14 side. A method for inserting the filter device 10 into the blood vessel 30 is the same as methods for inserting common catheters. It is judged by confirming the positions of the slide rings 23 and 24 by X-ray irradiation whether or not the filter device 10 is inserted into a desired position of the blood vessel 30.

When the distal end side of the catheter 11, i.e., the slide rings 23 and 24, reach a desired position of the blood vessel 30, the catheter 11 is drawn back to the proximal end side with respect to the shaft 12 on the proximal end side of the filter device 10, i.e., the outside of the body, whereby the distal end guide 14 is separated from the distal end of the catheter 11 and the catheter 11 is further drawn back to the proximal end side, so that the filter 13 in the contracted state is exposed to the outside from the distal end of the catheter 11. The catheter 11 drawn back to the proximal end side is completely drawn out to the outside of the body.

The movement of the peripheral edge of the opening 21 which is the proximal end side of the filter 13 in the longitudinal direction with respect to the shaft 12 is prevented by the slide ring 24 and the stoppers 25 and 26. The distal end of the filter 13 is slidable to the slide ring 24 side along the shaft 12 together with the slide ring 23 and the slide ring 23 may slide to the slide ring 24 side together with the catheter 11 due to friction with the inner wall of the catheter 11. However, the abutting of the slide ring 23 on the stopper 27 prevents the slide ring 23 from moving closer to the slide ring 24 by a distance equal to or more than a distance required for changing to the expanded state to excessively bend or damage the filter 13.

As illustrated in FIG. 3, due to the fact that the filter 13 in the contracted state is exposed to the outside from the lumen 20 of the catheter 11, the filter 13 is elastically returned to be expanded. Due to the fact that the filter 13 is changed to the expanded state from the contracted state, the slide ring 23 slides along the shaft 12 until the slide ring 23 abuts on or is brought close to the stopper 27 but the slide ring 24 does not move in the longitudinal direction of the shaft 12. Therefore, the filter 13 is expanded without moving from the position of the slide ring 24 confirmed by X-ray irradiation. Since both the slide rings 23 and 24 are rotatable about the shaft 12 as the axis, the filter 13 in the expanded state rotates with respect to the shaft 13 following the inner wall shape of the blood vessel 30.

Although not illustrated in each view, after the filter 13 is indwelled in the expanded state at a desired position of the blood vessel 30, a balloon catheter or the like is inserted into the blood vessel 30, and then an operation of expanding or excising a stenosis part (embolus) is performed. Due to the fact that the filter 13 is indwelled on the downstream side of the blood flow relative to the stenosis part, an embolus separated from the stenosis part by the operation is captured by the filter 13.

When the filter 13 is collected from the blood vessel 30, a procedure opposite to the above-described procedure is performed. More specifically, the catheter 11 is sent to the distal end side from the proximal end side of the shaft 12, and then the filter 13 in the expanded state is housed in the lumen 20 of the catheter 11. Due to the fact that the distal end of the catheter 11 moves to the distal end side while abutting on the peripheral edge of the opening 12 of the filter 13, the filter 13 is elastically contracted corresponding to the lumen 20. In connection with the contraction, the filter 12 is elastically changed from the expanded state to the contracted state. In a state where the filter 13 is housed in the lumen 20, the filter device 10 is drawn out of the blood vessel 30.

Operational Effects of First Embodiment

According to the filter device 10 of the first embodiment, the slide ring 23 provided on the distal end side of the filter 13 is rotatable about the shaft 12 as the axis and movable along the shaft 12 and the slide ring 24 provided on the proximal end side of the filter 13 is rotatable about the shaft 12 as the axis and the movement thereof in the longitudinal direction with respect to the shaft 12 is prevented. Therefore, even when the filter 13 is located at a desired position of the blood vessel 30, and then the catheter 11 is drawn back to the proximal end side, the filter 13 can be certainly placed at a desired position of the blood vessel 30 without causing positional deviation of the filter 13.

Moreover, the stopper 27 is fixed to the shaft 12 between the slide rings 23 and 24, and therefore, when the shaft 12 is further pressed to the distal end side, the proximal end side of the filter may be twisted. However, the abutting of the slide ring 23 on the stopper 27 prevents the slide ring 23 from moving closer to the slide ring 24 by a distance equal to or more than a distance required for changing to the expanded state to excessively bend or damage the filter 13.

Modification of First Embodiment

In the first embodiment described above, the stopper 27 is fixed to the shaft 12 between the slide rings 23 and 24. However, when the filter 13 contains a material which is hard to be bent or hard to be damaged, for example, the stopper 27 may not be provided.

Moreover, in the first embodiment described above, due to the fact that the slide ring 24 provided in the shaft 12 is held between the stoppers 25 and 26, the slide ring 24 is rotatable about the shaft 12 as the axis and the movement thereof in the longitudinal direction with respect to the shaft 12 is prevented. However, the proximal end side fixing portion according to the present invention may be realized by a different configuration. For example, the shaft 12 may be partially deformed into a convex shape so that the slide ring 24 cannot move in the longitudinal direction.

Moreover, in the first embodiment described above, although the filter 13 has a conical shape which has the opening 21 on the proximal end side and in which the diameter decreases toward the distal end side, so that the distal end side is closed, the filter 13 may have other shapes, such as a dome shape and a hemispherical shape, for example.

Moreover, in the first embodiment described above, although the slide rings 23 and 24 are detectable by X-rays, the stoppers 25, 26, and 27 and the distal end guide 14 may be configured to be detectable by X-rays, in place of the slide rings 23 and 24.

Moreover, in the filter device 10 described above, the filter 13 may be formed of a flexible material and a core material may be provided along the peripheral edge of the opening 21 of the filter 13. The core material is elastically deformed so as to be housed in the lumen 20 of the catheter 11. In the state where the core material is elastically deformed and the filter 13 is bent (contracted state), the filter 13 can be housed in the lumen 20 of the catheter 11. When the filter 13 comes out to the outside of the lumen 20, the core material is elastically returned to be an annular shape. In connection therewith, the entire shape of the filter 13 becomes a conical shape.

Moreover, the filter device 10 described above may be used not only in a carotid artery region but in a coronary artery region and a shunt region.

Second Embodiment

In a second embodiment, a predetermined number of thin wires having a shape memory property are knitted in a mesh shape in the filter 13 according to the first embodiment. Other configurations are the same as those of the first embodiment and the members denoted by the same reference numerals as those of the first embodiment are the same members.

Figure 4:
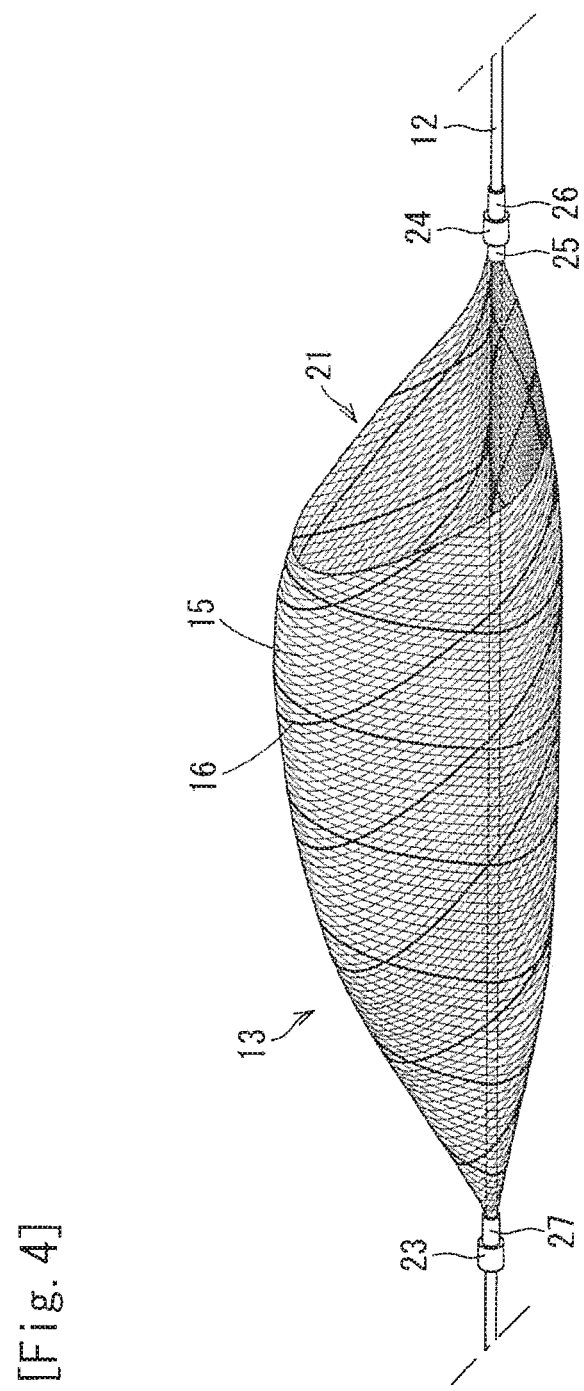
FIG. 4 is a perspective view illustrating an expanded state of a filter 13 according to a second embodiment.

As illustrated in FIG. 4, the filter 13 is formed into a conical bag shape by knitting a predetermined number (for example, 72) of thin wires having a shape memory property in a mesh shape. Therefore, the peripheral wall of the filter 13 is formed into a net shape. The thin wires configuring the filter 13 include first thin wires 15 having a shape memory property and two second thin wires 16 containing a radiation ray detection material which is detectable by radiation. In FIG. 4, the first thin wire 15 is illustrated by a thin line and the second thin wires 16 are illustrated by a thick line for convenience of description.

The filter 13 is knitted to a conical bag shape by knitting the first thin wires 15 (e.g., seventy thin wires 15) and the two second thin wires 16 individually let out from bobbins around which the seventy first thin wires 15 and the two second thin wires 16 are individually wound by a known knitting method (mesh knitting). The two second thin wires 16 are disposed so as to be knitted crossing to each other in the filter 13.

When the filter 13 knitted in a conical shape is changed to an expanded state, each of the first thin wires 15 and the second thin wires 16 is in a spiral state on the peripheral wall of the filter 13. More specifically, the one first thin wire 15 or the one second thin wire 16 extends from the distal end of the conical shape to the opening 21 spirally turning around the peripheral wall of the conical-shaped filter 13. The two second thin wires 16 cross to each other at a plurality of places on the peripheral wall of the filter 13. Therefore, in a radioscopic image (X-ray fluoroscopic image) obtained by irradiating the filter 13 expanded in a conical shape with radiation (usually, X-rays), the two second thin wires 16 which each form a spiral shape and which cross to each other appear. In the expanded state, both the two second thin wires 16 appear in a radioscopic image so as to cross to each other at an obtuse angle with respect to the shaft 12.

When the filter 13 is not in the expanded state, e.g., in the contracted state, the two second thin wires 16 appear in a radioscopic image so as to cross to each other at an acute angle with respect to the shaft 12 as compared with the angle in the expanded state, for example. Moreover, when the filter 13 is not in a perfect expanded state, the two second thin wires 16 do not appear in a radioscopic image in a state where the two second thin wires 16 cross to each other while turning around the peripheral wall of the conical-shaped filter 13 in a spiral shape. Therefore, it can be judged based on the state of the two second thin wires 16 in a radioscopic image whether or not the filter 13 is in the expanded state.

The first thin wire 15 in the filter 13 is not particularly limited insofar as a shape memory property is imparted. For example, superelastic alloys, such as a nickel-titanium steel wire, high-tensile steel wires for springs, metal wires, such as a piano wire, synthetic resin having relatively high rigidity, such as polyamide and fluororesin, and the like are preferably used.

Figure 5:
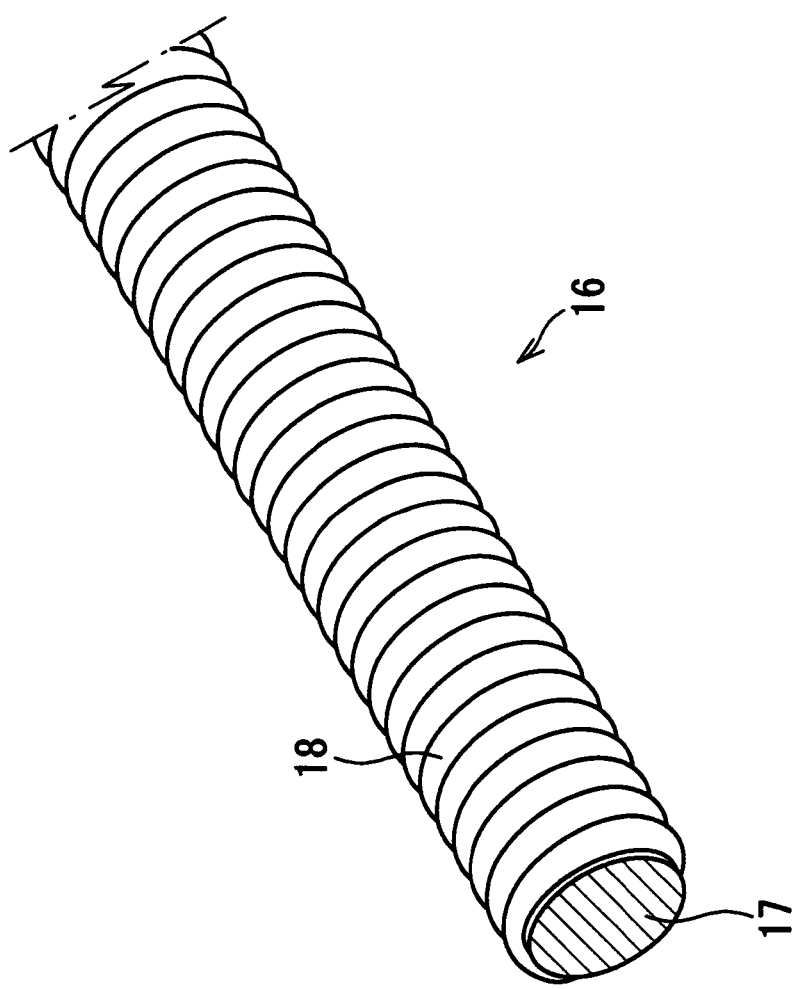
FIG. 5 is a perspective view illustrating an example of a second wire material 16 forming the filter 13 according to the second embodiment.

The second thin wire 16 is formed by winding a second wire 18 having radiopacity around the perimeter of a first wire 17 having the same shape memory property as that of the first thin wire 15 in a spiral shape as illustrated in FIG. 5. For example, a nickel-titanium steel wire is used as the first wire 17 and a tungsten wire is used as the second wire 18. The second wire 18 may be densely wound or wound at intervals on the periphery of the first wire 17. Due to the fact that the second wire 18 is densely wound, the second wire 18 is easily visually recognized in a radioscopic image. Or, due to the fact that the second wire 18 is wound at intervals, the shape memory property of the first wire 17 is hard to be blocked.

In the filter 13, the distal end portion is connected to the shaft 12 through the slide ring 23 and a part in the peripheral edge of the opening 21 is connected to the shaft 12 through the slide ring 24. The slide rings 23 and 24 are ring-shaped members containing members detectable by X-rays, such as stainless steel, and the shaft 12 is inserted into and passed through the internal space of each of the slide rings 23 and 24. The filter 13 and the slide rings 23 and 24 are bonded to each other by welding or with adhesives.

The slide ring 23 is rotatable about the shaft 12 as the axis and is slidable in the longitudinal direction with respect to the shaft 12. The distal end of the filter 13 bonded to the slide ring 23 is rotatable about the shaft 12 as the axis together with the slide ring 23 and is slidable in the longitudinal direction with respect to the shaft 12.

The slide ring 24 is held between a pair of stoppers 25 and 26 fixed to the distal end side of the shaft 12. The stoppers 25 and 26 are ring-shaped members containing stainless steel or the like and are fixed to the shaft 12 in a state where the shaft 12 is inserted into and passed through the internal space. The stoppers 25 and 26 do not rotate with respect to the shaft 12 and do not move in the longitudinal direction. The slide ring 24 held between the stoppers 25 and 26 is rotatable about the shaft 12 as the axis and the movement of the slide ring 24 in the longitudinal direction with respect to the shaft 12 is prevented.

A peripheral edge portion of the opening 21 of the filter 13 fixed to the slide ring 24 is rotatable about the shaft 12 as the axis and the movement thereof in the longitudinal direction with respect to the shaft 12 is prevented.

The shaft 12 is provided with the stopper 27 between the slide rings 23 and 24. The stopper 27 is a ring-shaped member containing stainless steel or the like and is fixed to the shaft 12 in a state where the shaft 12 is inserted into and passed through the internal space. The stopper 27 does not rotate with respect to the shaft 12 and does not move in the longitudinal direction. The stopper 27 is disposed at a position where the slide ring 24 abuts on or is brought close to the stopper 27 in the filter 13 in the expanded state. Due to the fact the slide ring 24 abuts on the stopper 27, the movement of the slide ring 23 to the slide ring 24 side relative to the position of the stopper 27 is prevented.

As the configuration in which the filter 13 is fixed to the shaft 12, known configurations other than the configuration described above may be adopted. Therefore, the combination and the arrangement with respect to the shaft 12 of the slide rings 23 and 24 and the stoppers 25, 26, and 27 may be altered as appropriate. Moreover, the filter 13 does not necessarily need to be a conical shape and other shapes, such as a dome shape and a cylindrical shape, may be adopted.

When the filter device 10 is used, it is confirmed under X-ray fluoroscopy whether or not the filter 13 is in the expanded state. More specifically, X-rays are emitted to the filter 13 located on the distal end side relative to the position of the slide ring 24 confirmed under X-ray fluoroscopy. Since the two second thin wires 16 knitted into the filter 13 contain a radiation ray detection material, the two second thin wires 16 are projected in an X-ray fluoroscopic image. As described above, it can be judged based on the shape of the projected two second thin wires 16, a crossing manner thereof with the shaft 12, and the like whether or not the filter 13 is in the expanded state.

Although not illustrated in each view, after the filter 13 is indwelled in the expanded state at a desired position of the blood vessel 30, a balloon catheter or the like is inserted into the blood vessel 30, and then an operation of expanding or excising a stenosis part (embolus) is performed. In this case, it is confirmed by an X-ray fluoroscopic image that the filter 13 is indwelled on the downstream side of the blood flow relative to a stenosis part and the opening 21 of the filter 13 is expanded in a circular shape in the blood vessel 30 and also the filter 13 is entirely expanded in a predetermined bag shape. Thus, an embolus separated from the stenosis part by the operation is certainly captured by the filter 13.

When the filter 13 is collected from the blood vessel 30, the catheter 11 is sent to the distal end side from the proximal end side of the shaft 12, and then the filter 13 in the expanded state is housed in the lumen 20 of the catheter 11 as described above. Due to the fact that the distal end of the catheter 11 moves to the distal end side while abutting on the peripheral edge of the opening 12 of the filter 13, the filter 13 is elastically contracted corresponding to the lumen 20. In connection with the contraction, the filter 13 is elastically changed from the expanded state to the contracted state. Also in this case, by emitting X-rays, it can be discriminated based on the shape of the two second thin wires 16, a crossing manner thereof with the shaft 12, and the like in an X-ray fluoroscopic image whether or not the filter 13 is in the contracted state. In a state where the filter 13 is housed in the lumen 20, the filter device 10 is drawn out of the blood vessel 30.

Operational Effects of Second Embodiment

According to the filter device 10 of the second embodiment, it can be certainly confirmed with a radioscopic image that the filter 13 is in the expanded state at a predetermined position in the blood vessel 30.

In a radioscopic image in which the filter 13 in the expanded state is projected, the second thin wires 16 form a spiral shape. Therefore, even when the filter 13 is projected from any direction, it is easily judged that the filter 13 is in the expanded state. Since the two second thin wires 16 cross to each other in the filter 13, it is easily and more accurately confirmed that the filter 13 is in the expanded state.

Moreover, in the filter 13 of the second embodiment, the two second thin wires 16 may be used in place of the two first thin wires 15 in the same manner as in a process of producing a filter by only using the first thin wire 15 having a shape memory property, and therefore the production of the filter 13 is facilitated.

Moreover, the second thin wire 16 has a configuration in which a second wire 18 which does not allow the transmission of radiation or attenuates radiation is wound around the circumference of a first wire 17 having a shape memory property, and therefore a function that the first wire 17 is returned to the expanded state is hard to be blocked by the second wire 18.

The number of the second thin wire 16 for use in the filter 13 is not limited to two. For example, in the case of the second thin wire 16 excellent in shape memory property and radiopacity, only one second thin wire 16 may be used. The number of the second thin wires 16 may be three or more. When two or more of the second thin wires 16 are used, the second thin wires 16 may not be knitted so as to cross to each other.

Modification of Second Embodiment

In the second thin wire 16 containing a radiation ray detection material, a tungsten wire containing tungsten which is a radiopaque substance can be used as the radiation ray detection material. The tungsten wire is inferior to the thin wire mentioned as an example of the first thin wire 15 in the shape memory property. Therefore, it is preferable to reduce the number of the tungsten wire to be used as much as possible so that the state change of the filter 13 is not blocked.

As the second thin wire 16, those in which a wire having a shape memory property is plated with a radiopaque metal as a radiation ray detection material may be used. Specifically, a nickel-titanium steel wire having a diameter of 0.03 mm is plated with gold to be used as the second thin wire 16. In this case, the thickness of a gold plating layer is set so that the shape memory property of the nickel-titanium steel wire is not impaired or desired radiopacity is achieved.

Third Embodiment

As illustrated in FIG. 6, a filter device 110 has a catheter 111, a shaft 112 (an example of the wire material) extended along the longitudinal direction of the catheter 111 in the catheter 111, a first support portion 113 and a second support portion 114 provided on the shaft 112, a filter 115 provided on the distal end side of the shaft 112, a distal end guide 116 provided at the distal end of the shaft 112, and a marker 117 provided on the distal end side of the catheter 111. The marker 117 has a first portion 118 and a second portion 119. The filter device 110 is inserted into a blood vessel from the distal end side of the catheter 111, and then the filter 115 is exposed from the distal end of the catheter 111, whereby the filter 115 in an expanded state is indwelled at a desired position of the blood vessel. FIG. 6 illustrates the filter device 110 when the filter 115 is in the expanded state.

The catheter 111 is a cylindrical member which can be inserted into a target blood vessel and has a lumen 120 (an example of the housing space, refer to FIGS. 7 and 8) passing through the distal end and the proximal end. The catheter 111 has flexibility which allows the catheter 111 to bend along a curve and a branch of a blood vessel. For the catheter 111, for example, flexible synthetic resin tubes of soft vinyl chloride resin, polyolefins, such as polyethylene and polypropylene, an ethylene-propylene copolymer and an ethylene-vinyl acetate copolymer, polyolefin elastomers, such as a mixture of polypropylene and polybutene, polyamide, fluororesin, such as PTFE and ETFE, a polyamide elastomer, a polyester elastomer, a polyurethane elastomer, a fluororesin-based elastomer, and the like; rubber tubes of silicon rubber, latex rubber, and the like; and the like are preferably used. The outer diameter and the length of the catheter 111 are set as appropriate according to the positions of a target blood vessel and a target lesion. Although not illustrated in each view, known structures, such as a handle held when operating the catheter 111, are provided on the proximal end side of the catheter 111.

The shaft 112 is a wire material extended along the longitudinal direction in the lumen 120 of the catheter 111. The shaft 112 has flexibility which allows the shaft 12 to bend along a curve and a branch of a blood vessel and rigidity which prevents buckling of the distal end side when the proximal end side is pressed in the longitudinal direction. As the shaft 112, a stainless steel wire, a piano wire, high-tensile steel wires for springs, superelastic metal wires, and the like are preferably used. The outer diameter and the length of the shaft 112 are set as appropriate according to the positions of a target blood vessel and a target lesion and the internal diameter and the length of the catheter 111.

The filter 115 is a net-like member which has an opening 121 on the first support portion 113 side and in which the second support portion 114 side is closed. The filter 115 is connected to the shaft 112 through the first support portion 113 and the second support portion 114. The filter 115 has a conical shape in which the diameter decreases toward the second support portion 114 side from the first support portion 113 side. The distal end side of the filter 115 is the vertex of the conical shape, the proximal end side of the filter 115 is the bottom surface side of the conical shape, and a portion equivalent to the bottom surface is the opening 121. The opening 121 has an annular shape having a diameter large than the diameter of the lumen 120 of the catheter 111. Therefore, in an expanded state described later, a portion having a diameter larger than the outer diameter of the space occupied by the lumen 120 is present in the outer shape of the filter 115. In the expanded state, the opening 121 is inclined with respect to the longitudinal direction of the shaft 112 and an end close to the shaft 112 is located on the proximal end side relative to an end apart from the shaft 112.

The filter 115 is elastically deformed so as to be housed in the lumen 120 of the catheter 111. In the state where the filter 115 is elastically deformed (contracted state), the filter 115 can be housed in the lumen 120 of the catheter 111. In the contracted state, the filter 115 is pressed against the inner surface of the catheter 111 defining the lumen 120. The filter 115 is pressed against the inner surface of the catheter 111, so that frictional force acts on both the filter 115 and the catheter 111. Thus, the catheter 111 and the filter 115 integrally rotate about the axis line in connection with an operation of the catheter 111. The filter 115 can move from the distal end of the catheter 111 to the outside while sliding on the inner surface of the catheter 111 in the contracted state by transmission of force of relatively moving the shaft 112 to the distal end side with respect to the catheter 111. When the filter 115 is moved to the outside from the lumen 120, the filter 115 is elastically returned to be a conical shape (expanded state).

For raw materials of the filter 115, superelastic alloys, such as a nickel-titanium steel wire, high-tensile steel wires for springs, metal wires, such as a piano wire, synthetic resin having relatively high rigidity, such as polyamide and fluororesin, and the like are preferably used, for example. The filter 115 is produced by knitting a linear metal or the like. The size of the filter 115, the diameter of the annular shape of the opening 121, and the like are set as appropriate according to the internal diameter of a target blood vessel or the catheter 111.

The first support portion 113 and the second support portion 114 are tubular bodies into and through the internal space of which the shaft 112 can be inserted and passed. The first support portion 113 and the second support portion 114 contain stainless steel or the like, for example. The first support portion 113 is held between a pair of stoppers 125 and 126 (an example of the first stopper) fixed to the distal end side of the shaft 112. The stoppers 125 and 126 are ring-shaped members containing stainless steel and the like and are fixed to the shaft 112 in the state where the shaft 112 is inserted into and passed through the internal space thereof. The stoppers 125 and 126 do not rotate with respect to the shaft 112 and do not move in the longitudinal direction. The first support portion 113 held between the stoppers 125 and 126 is rotatable about the shaft 112 as the axis and the movement of the first support portion 113 in the longitudinal direction with respect to the shaft 112 is prevented. The peripheral edge of the opening 121 of the filter 115 fixed to the first support portion 113 is rotatable about the shaft 112 as the axis and the movement thereof in the longitudinal direction with respect to the shaft 112 is prevented.

The shaft 112 is provided with a stopper 127 (an example of the second stopper) between the first support portion 113 and the second support portion 114. The stopper 127 is a ring-shaped member containing stainless steel or the like and is fixed to the shaft 112 in a state where the shaft 112 is inserted into and passed through the internal space thereof. The stopper 127 does not rotate with respect to the shaft 112 and does not move in the longitudinal direction. The stopper 127 is disposed at a position where the second support portion 114 abuts on or is brought close to the stopper 127 in the filter 115 in the expanded state. The second support portion 114 is rotatable about the shaft 112 as the axis and is movable in the longitudinal direction with respect to the shaft 112. Due to the fact that the second support portion 114 abuts on the stopper 127, the movement of the second support portion 114 to the first support portion 113 side relative to the position of the stopper 127 is prevented.

The filter 115 is bonded to the first support portion 113 and the second support portion 114 by welding or with adhesives. The peripheral edge of the opening 121 of the filter 115 bonded to the first support portion 113 is rotatable about the shaft 112 as the axis together with the first support portion 113. The distal end of the filter 115 bonded to the second support portion 114 is rotatable about the shaft 112 as the axis together with the second support portion 114 and is slidable in the longitudinal direction with respect to the shaft 112.

Since the first support portion 113 is bonded to the peripheral edge of the opening 121 of the filter 115, the shaft 112 inserted into and passed through the first support portion 113 is located at a position other than the center of the opening 121 of the filter 115. The filter 115 in a conical shape when the filter 115 is in the expanded state is in a state where the opening 121 is extended in a predetermined direction from the shaft 112. More specifically, there are a direction in which the opening 121 is present with respect to the shaft 112 and a direction in which the opening 121 is not present with respect to the shaft 112. In other words, the filter 115 in the expanded state is located in a direction deviated with respect to the axis line of the shaft 112.

The distal end guide 116 is fixed to the distal end of the shaft 112. The distal end guide 116 is projected along the axis line of the shaft 112 from the distal end of the shaft 112. The distal end guide 116 has a fitting portion 128 fitted to the distal end of the catheter 111 and a guide portion 129 projected from the fitting portion 128. The fitting portion 128 contains a synthetic resin. When a part of the fitting portion 128 enters the lumen 120 in the distal end of the catheter 112, the fitting portion 128 is fitted to the catheter 111 in a state where the distal end of the lumen 120 is sealed. The guide portion 129 is obtained by winding stainless steel in a spiral shape and is elastically curved along a curve and a branch of a blood vessel.

As illustrated in FIG. 9, the marker 117 is provided on the distal end side of the outer peripheral surface of the catheter 111. The marker 117 is detectable by X-rays. The marker 117 contains a first portion 118 continuous in the circumferential direction of the catheter 111 and a second portion 119 extended along the longitudinal direction of the catheter 11 from a part in the circumferential direction of the first portion 118.

FIG. 10(*a*) to FIG. 10(*d*) are views schematically illustrating the marker 117 formed on the catheter 111. FIG. 10(*a*) to FIG. 10(*d*) each illustrate the distal end of the catheter 111 viewed from four different directions orthogonal to the longitudinal direction of the catheter 111. The four different directions each are directed to the axis line of the catheter 111 from different positions at each 90° about the axis line of the catheter 111. In other words, FIG. 10(*b*) illustrates a state where the distal end side of the catheter 111 illustrated in FIG. 10(*a*) is rotated at each 90° about the axis line of the catheter 111.

As illustrated in FIG. 9 and FIG. 10(*a*) to FIG. 10(*d*), the first portion 118 is located on the distal end side of the catheter 111 relative to the second portion 119. The first portion 118 has an annular shape continuous in the circumferential direction about the axis line of the catheter 111. In the first portion 118, a length 118*a* along the longitudinal direction of the catheter 111 is fixed. The length 118*a* is not particularly limited and is shorter than an outer diameter 111*a* of the catheter 111, for example. Therefore, when the first portion 118 is visually recognized from the direction orthogonal to the longitudinal direction of the catheter 111, the first portion 118 has a thin and narrow rectangular shape extending in a direction orthogonal to the longitudinal direction of the catheter 111. The length of the rectangular shape (a length 118*b* in a direction orthogonal to the longitudinal direction of the catheter 111) is the same as the outer diameter 111*a* of the catheter 111. As illustrated in FIG. 10(*a*) to FIG. 10(*d*), even when viewed from any of the four different directions, the first portion 118 is visually recognized to have the same shape.

The second portion 119 has a rectangular shape extending along the longitudinal direction toward the proximal end side of the catheter 111 from the edge on the proximal end side of the catheter 11 in the first portion 118. In the second portion 119, a length 119*a* along the circumferential direction of the catheter 111 is fixed. The length 119*a* is shorter than the half of the length of the circumference along the circumferential direction of the external surface of the catheter 111. A length 119*c* along the longitudinal direction of the second portion 119 is not particularly limited and is sufficiently longer than the length 119*a*, for example. Therefore, when the second portion 119 is visually recognized from a direction orthogonal to the longitudinal direction of the catheter 111, the second portion 119 has a rectangular shape extending in the longitudinal direction of the catheter 111.

As illustrated in FIG. 10(*a*) to FIG. 10(*d*), even when viewed from any of the four directions, the length 119*c* along the longitudinal direction of the second portion 119 is the same. On the other hand, a length 119*b* of the second portion 119 varies depending on the four different directions. The relative positional relationship of the second portion 119 and the first portion 118 also varies.

In detail, as illustrated in FIG. 10(*a*), the second portion 119 extends in the longitudinal direction from the upper end of the first portion 118. In other words, in the case of an inverted L-shape in which the first portion 118 does not extend upward relative to the upper end of the second portion 119, the second portion 119 is located on the upper side (on the upper side in FIG. 10(*a*)) of the catheter 111. Therefore, when the filter 115 housed in the catheter 111 in this state is changed to the expanded state, the filter 115 is expanded upward (upward in FIG. 10) with respect to the shaft 112.

As illustrated in FIG. 10(*b*) and FIG. 10(*d*), the second portion 119 extends in the longitudinal direction from the vicinity of the center in the vertical direction of the first portion 118. In other words, in a case of a lateral T-shape in which the first portion 118 extends upward relative to the upper end of the second portion 119 and the first portion 118 extends downward relative to the lower end of the second portion 119, the second portion 119 is located on the front side (front surface side of the sheet of FIG. 10(*b*)) or the back side (back surface side of the sheet of FIG. 10(*d*)) of the catheter 111. In a state where the catheter 111 is caused to stay still, the state illustrated in FIG. 10(b) and the state illustrated in FIG. 10(d) cannot be distinguished from each other. However, due to the fact that the catheter 111 is rotated at about 90° in a fixed direction in the circumferential direction, the states can be distinguished based on whether or not the lateral T-shape is changed to the inverted L-shape illustrated in FIG. 10(a). When the filter 115 housed in the catheter 111 in each state is changed to the expanded state, the filter 115 is expanded in the frontward direction or in the backward direction (directed to the front surface or directed to the back surface of the sheet in FIG. 10) with respect to the shaft 12.

As illustrated in FIG. 10(c), the second portion 119 extends in the longitudinal direction from the lower end of the first portion 118. In other words, in the case of an L-shape in which the first portion 118 does not extend downward relative to the lower end of the second portion 119, the second portion 119 is located on the lower side (lower side in FIG. 10(c)) of the catheter 111. Therefore, when the filter 115 housed in the catheter 111 in this state is changed to the expanded state, the filter 115 is expanded downward (downward in FIG. 10) with respect to the shaft 112.

The first portion 118 and the second portion 119 are detectable by X-rays. The first portion 118 is formed of metal. As raw materials of the first portion 118, metals, such as gold, platinum, iridium, palladium, and tantalum, or alloys thereof are preferably used, for example. The second portion 119 is formed of resin. As raw materials of the second portion 119, resin containing inorganic materials detectable by X-rays is mentioned. As the inorganic materials, bismuth oxide, tungsten, and the like are preferably used. As the resin, thermoplastic elastomers, such as a polyamide elastomer, a polyethylene elastomer, and a polystyrene elastomer, are preferably used.

A method for forming the first portion 118 and the second portion 119 on the distal end portion of the catheter 111 in the filter device 110 is described below. The first portion 118 has a ring shape, for example, and is externally inserted into the catheter 111 to be attached thereto.

The formation of the second portion 119 includes a molding process of molding a resin plate and a fixing process of fixing the resin plate to the distal end portion of the catheter 111. In the molding process, the resin plate serving as the second portion 119 is molded. Examples of the plate molding method include methods generally used as methods for molding synthetic resin, such as extrusion molding and injection molding. In the fixing process, the resin plate is disposed on the external surface of the distal end portion of the catheter 111. A general heat shrinkable tubular body is fitted to the outside of the plate disposed on the external surface of the catheter 111. The resin plate is fixed to the external surface of the catheter 111 by heating. Thus, the second portion 119 is formed.

As methods for forming the first portion 118 and the second portion 119, different methods may be adopted. For example, the first portion 118 and the second portion 119 may be integrally fixed to the external surface of the catheter 111 by a tubular body having heat shrinkable properties. The first portion 118 and the second portion 119 may be buried in the catheter 111 or may be integrally molded when the catheter 111 is molded.

[Directions for Use of Filter Device 110]

Hereinafter, the directions for use of the filter device 10 are described with reference to FIG. 7 to FIG. 10. In FIGS. 7 and 8, only a visible outline is illustrated for the filter 115.

The filter 115 is housed in the lumen 120 of the catheter 111 so as to hold an arbitrary relative positional relationship with respect to the catheter 111. For example, the filter 115 is housed in the lumen 120 in the contracted state so that the position of the filter 115 with respect to the axis line of the shaft 112 is in agreement with the position of the second portion 119 of the marker 117 with respect to the axis line of the shaft 112. The filter 115 comes out to the outside of the lumen 120 to change the state to the expanded state from such a contracted state. In other words, when the filter 115 is housed in the lumen 120 so that the filter 115 is located on the upper side of FIG. 6 with respect to the shaft 112 in the expanded state, the filter 115 is similarly located on the upper side of FIG. 6 with respect to the shaft 112 and the catheter 111 is fixed to a rotation attitude (refer to FIG. 10(a)) in which the second portion 119 of the marker 117 is located on the upper side of FIG. 6 with respect to the shaft 112, and then the filter 115 is housed in the lumen 120. Thus, in the housed state, the position of the filter 115 with respect to the shaft 112 and the position of the second portion 119 with respect to the shaft 112 are in agreement with each other.

As illustrated in FIG. 7, the filter device 110 is inserted into the blood vessel 30 in a state where the filter 115 is changed to the contracted state to be housed in the lumen 120 of the catheter 111 and the distal end guide 116 is fitted to the distal end of the catheter 111. The filter device 110 is inserted into the blood vessel 30 from the distal end guide 116 side but a method for inserting the filter device 110 into the blood vessel 30 is the same as methods for inserting common catheters. It is judged by confirming the positions of the first support portion 113 and the second support portion 114 by X-ray irradiation whether or not the filter device 110 is inserted into a desired position of the blood vessel 30.

When the distal end side of the catheter 111 reaches a desired position of the blood vessel 30, the proximal end side of the catheter 111 is rotated about the longitudinal direction as the axis in order to adjust the rotation attitude of the catheter 111. When the catheter 111 is rotated, the filter 115 housed in the lumen 120 also rotates due to the frictional force with the inner surface of the catheter 111. During the rotation, the relative positional relationship between the catheter 111 and the filter 115 does not vary. For example, when the filter 115 is to be indwelled in a curved portion 31 of the blood vessel 30 as illustrated in FIG. 8, the filter 115 is preferably located on the outside of the curve in the curved portion 31 relative to the shaft 112. Therefore, an operator rotates the proximal end side of the catheter 111 to adjust so that the filter 115 is located on the outside of the curve in the curved portion 31.

The rotation attitude of the catheter 111 in the curved portion 31 is judged by confirming the shapes of the first portion 118 and the second portion 119 by X-ray irradiation. In order to locate the filter 115 on the outside of the curve of the blood vessel 30, the catheter 111 is rotated so that the second portion 119 is located on the outside of the curve of the curved portion 31 of the blood vessel 30 as illustrated in FIG. 7. More specifically, the catheter 111 is rotated so that the second portion 119 extends in the longitudinal direction from the end of the outside of the curve of the first portion 118 as illustrated in FIG. 10(a), in other words, the marker 117 is visually recognized to be in a state where the first portion 118 does not extend from the end of the outside of the curve of the second portion 119 to the outside of the curve.

The catheter 111 is changed to the rotation attitude illustrated in FIG. 7, and then the catheter 111 is drawn back to the proximal end side with respect to the shaft 112 on the proximal end side of the filter device 110, i.e., the outside of the body, whereby the distal end guide 116 is separated from the distal end of the catheter 111 and the filter 115 in the contracted state is exposed to the outside from the distal end of the catheter 111. The catheter 111 drawn back to the proximal end side with respect to the shaft 112 is completely drawn out to the outside of the body. Thus, the filter 115 is exposed from the catheter 111 with a desired direction. The catheter 111 may be pressed out to the outside from the distal end of the catheter 111 by pressing out the shaft 112 with respect to the catheter 111 instead of drawing back the filter 115.

The movement of the peripheral edge of the opening 121 which is the proximal end side of the filter 115 in the longitudinal direction with respect to the shaft 112 is prevented by the first support portion 113 and the stoppers 125 and 126. The distal end of the filter 115 is slidable to the first support portion 113 side along the shaft 112 together with the second support portion 114 and the second support portion 114 may slide to the first support portion 113 side together with the catheter 111 due to friction with the inner wall of the catheter 111. However, the abutting of the second support portion 114 on the stopper 127 prevents the second support portion 114 from moving closer to the first support portion 113 by a distance equal to or more than a required distance for changing to the expanded state to excessively bend or damage the filter 115.

As illustrated in FIG. 8, due to the fact that the filter 115 in the contracted state is exposed to the outside from the lumen 120 of the catheter 111, the filter 115 is elastically returned to be changed to the expanded state. The filter 115 is located on the outside of the curve of the bent portion 31 with respect to the shaft 112 to be changed to the expanded state in the blood vessel 30. Due to the fact that the filter 115 is changed to the expanded state from the contracted state, the second support portion 114 slides along the shaft 112 until the second support portion 114 abuts on or is brought close to the stopper 127 but the first support portion 113 does not move in the longitudinal direction of the shaft 112. Therefore, the filter 115 is changed to the expanded state without moving from the position of the first support portion 113 confirmed by X-ray irradiation. The filter 115 which is located on the outside of the curve of the bent portion 31 and is changed to the expanded state is hardly pressurized by the shaft 112 located on the inside of the curve and the opening 121 is located along the inner wall of the blood vessel 30.

Although not illustrated in each view, after the filter 115 is indwelled in the expanded state in the curved portion 31 of the blood vessel 30, a balloon catheter or the like is inserted into the blood vessel 30, and then an operation of expanding or excising a stenosis part (embolus) is performed. Due to the fact that the filter 115 is indwelled on the downstream side of the blood flow relative to the stenosis part, an embolus separated from the stenosis part by the operation is captured by the filter 115.

When the filter 115 is collected from the blood vessel 30, a procedure opposite to the above-described procedure is performed. More specifically, the catheter 111 is sent to the distal end side from the proximal end side of the shaft 112, and then the filter 115 in the expanded state is housed in the lumen 120 of the catheter 111. Due to the fact that the distal end of the catheter 111 moves to the distal end side while abutting on the peripheral edge of the opening 121 of the filter 115, the filter 115 is elastically contracted corresponding to the lumen 120. In connection with the contraction, the filter 115 is elastically changed from the expanded state to the contracted state. In the state where the filter 115 is housed in the lumen 120, the filter device 110 is drawn out of the blood vessel 30. When the filter 115 is collected from the blood vessel 30, the position of the filter 115 and the position of the second portion 119 are not in agreement with each other.

Operational Effects of Third Embodiment

According to the filter device 110 of the third embodiment, the first portion 118 and the second portion 119 provided on the distal end side of the catheter 111 are detected by X-rays in the blood vessel 30 and the position of the filter 115 with respect to the shaft 112 can be judged based on the shape of the detected second portion 119. Therefore, the rotation attitude of the catheter 111 can be adjusted so that the filter 115 is expanded in a desired direction in the blood vessel 30.

Moreover, the first portion 118 is formed of metal and, on the other hand, the second portion 119 is formed of a substance in which an inorganic material is mixed into resin. The concentration and the type of the inorganic material can be varied. The concentration and the type of the inorganic material affect imaging by X-rays. In other words, how the second portion 119 looks in an X-ray projected image varies depending on the concentration and the type of the inorganic material. Thus, the first portion 118 and the second portion 119 can be easily distinguished from each other.

Moreover, the second portion 119 is extended along the longitudinal direction of the catheter 111. However, since the second portion 119 is formed of resin, the flexibility of the catheter 111 is not impaired in the distal end portion of the catheter 111.

Moreover, since the filter 115 rotates in connection with the rotation about the longitudinal direction of the catheter 111 as the axis due to the contact with the inner surface defining the lumen 120 of the catheter 111, special members and structures for rotating the filter 115 in connection with the rotation of the catheter 111 are not required.

Moreover, since the length 119a along the circumferential direction of the second portion 119 is shorter than the length of the half of the circumference along the circumferential direction of the external surface of the catheter 111, the position in the circumferential direction of the second portion 119 is easily grasped.

Moreover, since the length 119c along the longitudinal direction of the second portion 119 is longer than the length 118a in the longitudinal direction of the first portion 118, the first portion 118 and the second portion 119 are easily distinguished from each other.

Modification of Third Embodiment

In the third embodiment described above, although the length 118a of the first portion 118 in the longitudinal direction of the catheter 111 is uniformly formed, the length 118a may not necessarily be fixed. Similarly, the length 119a of the second portion 119 may not be fixed. For example, a shape may be acceptable in which the second portion 119 can be visually recognized as a triangular shape or a circular shape in the state illustrated in FIG. 10(b).

Moreover, the entire regions of the first portion 118 and the second portion 119 do not necessarily need to be X-ray opaque and a region which allows transmission of X-rays may be formed inside.

Moreover, both the first portion 118 and the second portion 119 may be formed of metal or may be formed of resin. Moreover, the first portion 118 may be formed of resin and the second portion 119 may be formed of metal.

Moreover, although the filter 115 and the shaft 112 are connected to each other by providing the first support portion 113 on the peripheral edge of the opening 121 of the filter 115 in the third embodiment described above, the filter 115 may be connected to the shaft 112 at positions other than the peripheral edge of the opening 121 insofar as the position is not the center of the opening 121 of the filter 115.

Moreover, although the filter 115 has a conical shape in the embodiment described above, the filter 115 may have other shapes, such as a hemispherical shape and a dome shape, for example. When the shaft 112 is connected at positions other than the center of the opening of the filter 115 of a hemispherical shape or a dome shape in the expanded state, the direction of a side where the opening is larger with respect to the shaft 112 of the filter 115 can be distinguished based on the shape of the marker 117 of the catheter 111 in the same manner as described above.

Moreover, the relative positional relationship between the filter 115 and the catheter 111 is held due to the frictional force generated by the contact of the filter 115 with the inner surface defining the lumen 120 of the catheter 111 in the filter device 110 described above. However, for example, the cross section of the internal space of the catheter 111 may be formed in a shape which is not point symmetry, such as an egg shape, and the relative position between the catheter 111 and the filter 115 may be held due to fitting between the cross section and the filter 115 in the contracted state.

REFERENCE SIGNS LIST

10 Filter device
11 Catheter
12 Shaft (Wire material)
13 Filter
15 First thin wire
16 Second thin wire (containing radiation detection material)
17 First wire
18 Second wire
20 Lumen (Housing space)
23 Slide ring (Slider)
24 Slide ring (Tubular body, Proximal end side fixing portion)
25, 26 Stopper (Second stopper, Proximal end side fixing portion)
27 Stopper (First stopper)
110 Filter device
111 Catheter
112 Shaft (Wire material)
113 First support portion
114 Second support portion
115 Filter
116 Distal end guide
117 Marker
118 First portion
119 Second portion
120 Lumen (Housing space)
121 Opening
125, 126 Stopper (First stopper)
127 Stopper (Second stopper)

The invention claimed is:

1. A filter device comprising:
a catheter having a housing space inside;
a wire material extended along a longitudinal direction of the catheter in the housing space of the catheter;
a distal end guide fixed to a distal end of the wire material, the distal end guide comprising:
a fitting portion configured to be fitted to a distal end of the catheter so as to seal the housing space, and
a guide portion projecting distally from the fitting portion;
a filter capable of changing a state between an expanded state in which the filter is exposed to a distal end side of the catheter to be expanded to an outer side relative to an outer shape of the catheter, and a contracted state in which the filter is elastically contracted from the expanded state so as to be housed in the housing space;
a slider that is attached to a distal end of the filter, the slider being rotatable about an axis of the wire material, and being movable along the wire material;
a slide ring that is attached to a proximal end of the filter, the slide ring being rotatable about the axis of the wire material, and being prevented from moving in the longitudinal direction with respect to the wire material;
a first stopper fixed to the wire material between the slider and slide ring, wherein the first stopper is disposed at a position where the slider abuts on or is brought close to the first stopper in the filter in the expanded state; and
second stoppers individually fixed to the wire material on a distal end side and a proximal end side with respect to the slide ring.

2. The filter device according to claim 1, wherein:
the filter has a conical shape that has an opening at the proximal end and in which a diameter decreases toward the distal end.

3. The filter device according to claim 1, wherein:
the slider and the slide ring are detectable by radiation.

4. A filter device comprising:
a catheter having a lumen therein;
a shaft extending through the lumen of the catheter in a longitudinal direction of the catheter;
a distal end guide fixed to a distal end of the shaft, the distal end guide comprising:
a fitting portion configured to be fitted to a distal end of the catheter so as to seal the lumen, and
a guide portion projecting distally from the fitting portion;
a filter;
a slider that is attached to a distal end of the filter, the slider being rotatable about the shaft and movable along the shaft; and
a slide ring that is attached to a proximal end side of the filter, the slide ring being rotatable about the shaft;
a first stopper fixed to the shaft between the slider and slide ring, wherein the first stopper is disposed at a position where the slider abuts on or is brought close to the first stopper in the filter in the expanded state; and
second stoppers individually fixed to the wire material on a distal end side and a proximal end side with respect to the slide ring,
wherein the shaft is slidable with respect to the catheter between:
a first state in which the filter, slider, and slide ring are housed in the lumen of the catheter, and the filter is in an elastically contracted state, and
a second state, in which the filter, slider, and slide ring are located outside the lumen of the catheter, and the filter is in an expanded state so as to extend outward relative to an outer surface of the catheter.

5. The filter device according to claim 4, wherein:
the filter has a conical shape which has an opening at the proximal end and in which a diameter decreases toward the distal end.

6. The filter device according to claim 4, wherein:
the slider and the slide ring are detectable by radiation.

\* \* \* \* \*

UNITED STATES PATENT AND TRADEMARK OFFICE
CERTIFICATE OF CORRECTION

PATENT NO. : 10,307,239 B2
APPLICATION NO. : 15/303440
DATED : June 4, 2019
INVENTOR(S) : Hiroki Watanabe It is certified that error appears in the above-identified patent and that said Letters Patent is hereby corrected as shown below:

In the Claims

Claim 4, Column 24, Lines 52-53:
Please delete "a slide ring that is attached to a proximal end side of the filter, the slide ring being rotatable about the shaft;".
Please insert -- a slide ring that is attached to a proximal end of the filter, the slide ring being rotatable about the shaft; --.

Signed and Sealed this
Third Day of September, 2019

Andrei Iancu
*Director of the United States Patent and Trademark Office*